(12) United States Patent
Silverberg et al.

(10) Patent No.: US 9,056,060 B2
(45) Date of Patent: *Jun. 16, 2015

(54) NON-REACTIVE ADHESIVE USEFUL IN TRANSDERMAL DRUG DELIVERY SYSTEM

(75) Inventors: Eric Silverberg, Clifton, NJ (US); Rama Chandran, Bridgewater, NJ (US); Paul Foreman, Somerville, NJ (US); Michael Philbin, Hopewell, NJ (US); Smita Shah, Edison, NJ (US)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/955,644

(22) Filed: Sep. 18, 2001

(65) Prior Publication Data

US 2002/0077437 A1    Jun. 20, 2002

Related U.S. Application Data

(60) Provisional application No. 60/234,248, filed on Sep. 19, 2000.

(51) Int. Cl.
| | |
|---|---|
| *A61F 13/02* | (2006.01) |
| *A61L 15/16* | (2006.01) |
| *A61F 13/00* | (2006.01) |
| *A61K 9/70* | (2006.01) |
| *C08F 20/54* | (2006.01) |
| *C08F 20/70* | (2006.01) |
| *C08F 26/02* | (2006.01) |
| *C08F 120/54* | (2006.01) |
| *C08F 120/70* | (2006.01) |
| *C08F 126/02* | (2006.01) |
| *C08F 136/00* | (2006.01) |
| *C08F 220/54* | (2006.01) |
| *C08F 220/70* | (2006.01) |
| *C08F 226/02* | (2006.01) |
| *C08F 236/00* | (2006.01) |
| *C08F 212/00* | (2006.01) |
| *C08F 216/12* | (2006.01) |
| *C08F 20/26* | (2006.01) |
| *C08F 220/26* | (2006.01) |
| *C08F 20/10* | (2006.01) |
| *C08F 220/10* | (2006.01) |
| *A61L 15/58* | (2006.01) |
| *C09J 133/06* | (2006.01) |

(52) U.S. Cl.
CPC .............. *A61K 9/7053* (2013.01); *A61K 9/7061* (2013.01); *A61L 15/58* (2013.01); *C09J 133/062* (2013.01)

(58) Field of Classification Search
CPC ........... C08F 2220/1825; C08F 220/14; C08F 220/18; C08F 220/06; C08F 8/30; C08G 18/0823; C08G 18/348; A61L 15/58; A61L 15/60; C09D 133/08; C09J 4/00; C09J 4/06; C09J 133/062; C09J 7/0225; A61K 9/7053; A61K 9/7061; A61Q 17/04; D06M 15/263; D06M 15/333; D06M 13/192; D06M 13/184; D06M 13/224; D06M 15/267
USPC .......................................... 424/448, 449, 443
See application file for complete search history.

(56) References Cited

U.S. PATENT DOCUMENTS

| | | | |
|---|---|---|---|
| 3,008,850 A | 11/1961 | Ulrich et al. | |
| 3,475,363 A | 10/1969 | Gander et al. | |
| 3,491,070 A | 1/1970 | Weaver | |
| 3,922,464 A | 11/1975 | Silver et al. | |
| 4,458,036 A | 7/1984 | Fesman | 521/107 |
| 4,514,524 A | 4/1985 | Fesman | 521/107 |
| 4,588,580 A * | 5/1986 | Gale et al. | 424/449 |
| 4,616,044 A | 10/1986 | Fesman | 521/107 |
| 4,655,767 A | 4/1987 | Woodard et al. | |
| 4,721,744 A | 1/1988 | Ishii et al. | 524/91 |
| 4,732,808 A * | 3/1988 | Krampe et al. | 428/355 CN |
| 4,814,168 A | 3/1989 | Sablotsky et al. | |
| 4,988,567 A * | 1/1991 | Delgado | 428/402 |
| 4,994,267 A * | 2/1991 | Sablotsky | 514/182 |
| 5,133,970 A | 7/1992 | Petereit et al. | |
| 5,186,938 A | 2/1993 | Sablotsky et al. | |
| 5,234,957 A | 8/1993 | Mantelle | |
| 5,380,779 A | 1/1995 | D'Haese | |
| 5,391,406 A * | 2/1995 | Ramharack et al. | 427/516 |
| 5,458,885 A * | 10/1995 | Muller et al. | 424/448 |
| 5,474,783 A * | 12/1995 | Miranda et al. | 424/448 |
| 5,560,491 A | 10/1996 | Romaniuk et al. | |
| RE35,474 E | 3/1997 | Woodard et al. | |
| 5,656,286 A * | 8/1997 | Miranda et al. | 424/449 |
| 5,723,534 A | 3/1998 | Murray | 524/590 |
| 5,730,999 A * | 3/1998 | Lehmann et al. | 424/443 |
| 5,827,505 A * | 10/1998 | Hughes et al. | 424/49 |
| 6,077,527 A * | 6/2000 | Tan et al. | 424/448 |
| 6,132,760 A * | 10/2000 | Hedenstrom et al. | 424/448 |

(Continued)

FOREIGN PATENT DOCUMENTS

| | | | |
|---|---|---|---|
| CA | 2455064 A1 | 3/2003 | |
| DE | 2 244 543 | 4/1974 | C07D 55/40 |

(Continued)

OTHER PUBLICATIONS

Aldrich Reference: Polymer Properties "Thermal Transitions of Homopolymers: Glass Transition & Melting Point."

(Continued)

*Primary Examiner* — Isis Ghali
(74) *Attorney, Agent, or Firm* — Sun Hee Lehmann

(57) ABSTRACT

An adhesive composition which lacks functional groups containing reactive hydrogen moieties and contains no post-polymerization chemical crosslinker finds use in transdermal drug delivery systems. The invention enables the administration of drugs containing a reactive functional group, which drugs have heretofore not been able to be administered by the transdermal route using conventional acrylic adhesives.

3 Claims, No Drawings

(56) References Cited

U.S. PATENT DOCUMENTS

| | | | |
|---|---|---|---|
| 6,139,866 A | 10/2000 | Chono et al. | |
| 6,239,228 B1 * | 5/2001 | Zajaczkowski et al. | 525/302 |
| 6,541,566 B1 * | 4/2003 | Farwaha et al. | 524/837 |
| 6,703,027 B2 | 3/2004 | Kurosawa et al. | |
| 2002/0077347 A1 | 6/2002 | Liu et al. | |
| 2002/0119187 A1 | 8/2002 | Cantor et al. | |
| 2002/0150613 A1 * | 10/2002 | Govil et al. | |
| 2004/0234584 A1 | 11/2004 | Muller et al. | |
| 2004/0241219 A1 | 12/2004 | Hille et al. | |
| 2006/0039960 A1 | 2/2006 | Cordes et al. | |
| 2006/0099242 A1 | 5/2006 | Garbe et al. | |

FOREIGN PATENT DOCUMENTS

| | | | |
|---|---|---|---|
| EP | 0297769 A1 | 1/1989 | |
| EP | 0 304 214 | 2/1989 | C08G 18/46 |
| EP | 0189873 B1 | 8/1991 | |
| EP | 0444354 A2 | 9/1991 | |
| EP | 0489524 A1 | 6/1992 | |
| EP | 531938 A1 * | 3/1993 | |
| EP | 0531938 A1 | 3/1993 | |
| EP | 0913445 A1 | 5/1999 | |
| GB | 955420 A | 4/1964 | |
| GB | 1044828 A | 10/1966 | |
| GB | 1081298 A | 8/1967 | |
| GB | 1168333 A | 10/1969 | |
| JP | S58138462 A | 8/1983 | |
| JP | 59181214 A | 10/1984 | |
| JP | 61-126020 | 6/1986 | |
| WO | WO 9608229 A3 * | 7/1996 | |
| WO | 9956782 A1 | 11/1999 | |
| WO | WO 03/018076 | 3/2003 | |

OTHER PUBLICATIONS

Kessel et al., "The diacetone acrylamide crosslinking reaction and its influence on the film formation of an acrylic latex." J. Coat. Technol. Res. 5(3) 285-297, 2008.

Kanios, David P., et al. "Effect of Non-Functional / Non-Reactive Pressure Sensitive Adhesives in Transdermal Drug Delivery Systems." Pressure Sensitive Tape Council, Proc. Annual Tech. Meeting, May 5-9, 2003.

Kim, Ju-Hyun, et al. "Effect of vehicles and pressure sensitive adhesives on the permeation of tacrine across hairless mouse skin." International Journal of Pharmaceutics, Elsevier Science B.V., vol. 196, issue 1, Feb. 25, 2000, pp. 105-113.

March, J., Advanced Organic Chemistry: reactions, mechanisms, and structure, 4th edition, John Wiley & Sons, 1992, p. 623.

Pfister, William, et al. "Silicone adhesives for transdermal drug delivery," Chemistry in Britain, The Royal Society of Chemistry, vol. 27, No. 1, Jan. 1991, pp. 43-46.

Paul Mentor; Bio-Rad, tech note 1156; Acylamide Polymerization—A Practical Approach, http://www.bio.vu.nl/geomicrob/protocols/DGGE/Acrylamide_polymerization.pdf.

* cited by examiner

NON-REACTIVE ADHESIVE USEFUL IN TRANSDERMAL DRUG DELIVERY SYSTEM This application claims benefit to the earlier filing date of provisional application No. 60/234,248, filed Sep. 19, 2000.

FIELD OF THE INVENTION

The invention relates to an adhesive composition. In particular, a non-reactive pressure sensitive adhesive which may advantageously be used in transdermal drug delivery applications. The invention also relates to a transdermal drug delivery system comprising the non-reactive adhesive.

BACKGROUND OF THE INVENTION

The continuous controlled delivery of drugs through the derma, i.e., skin, provides many advantages over other routes of administration. Transdermal drug delivery is a comfortable, convenient, and noninvasive alternative to other means of drug delivery such as by ingesting medication at fixed time intervals orally or by way of subcutaneous injection. Transdermal drug delivery systems not only allow the controlled release of a pharmaceutical product in a sustained release fashion, but reduce side effects such as gastrointestinal irritation, avoid hepatic first-pass inactivation, poor or erratic absorption from the gastrointestinal tract, and inactivation by the gastrointestinal fluids. Transdermal drug delivery also makes possible a high degree of control over blood concentrations of any particular drug. These advantages enhance patient compliance and improve the safety and efficacy of medications.

In transdermal drug delivery systems, drugs are delivered from a patch applied to the skin with a pressure sensitive adhesive. Useful adhesives are permanently tacky at room temperature, hold the transdermal system to the skin with gentle pressure, and can be easily removed without causing pain or depositing adhesive residue. Devices for transdermal delivery of drugs generally fall into either the category of liquid reservoir patches or matrix patches. The simplest form of matrix patch uses the adhesive itself as the carrier for a drug. In a liquid reservoir patch, the drug is dissolved or dispersed in a liquid reservoir compartment, either totally covered by a rate controlling membrane, or in a polymer matrix. While reservoir systems may use only a peripheral adhesive ring for attachment to the skin surface, a face adhesive which coats both the drug releasing surface and the area surrounding it is often used. Thus, in both matrix- and reservoir-type patches ingredients formulated into the transdermal delivery device, i.e., drugs and various excipients including cosolvents and skin penetration enhancers, must diffuse through the skin contact adhesive in reservoir-type systems and diffuse from the adhesive in matrix-type systems.

Some adhesives may, however, chemically react with various drugs, skin penetration enhancers and excipients in the transdermal system. For example, basic amine functional drugs can react with the acidic moieties of an acrylic adhesive causing a lack of adhesion and tack even before the device is applied to the patient's skin. Moreover, the reactivity of active ingredients within a transdermal drug delivery system with the polymer backbone or side group and with residual monomer could cause degradation and/or binding of the drug and, therefore, is a threat to sustained release and limits the application of this technology. A second area of concern to transdermal patch formulators is the formation of new compounds within the patch as a result of a chemical reaction between the active ingredients and the adhesive. These new compounds may be physiologically active in the body and cause deleterious effects.

The known advantages of continuous transdermal drug delivery devices has prompted the development of transdermal drug delivery systems for the administration of a variety of drugs. While acrylic adhesives for transdermal applications are known, and a number of transdermal drug delivery systems are currently available commercially, there remains a need in the art for a non-reactive adhesive composition for use in transdermal drug delivery systems so that this technology can be extended and used as a delivery option for an even broader range of drugs.

SUMMARY OF THE INVENTION

The invention provides a non-reactive adhesive composition useful in transdermal drug delivery systems.

One aspect of the invention is directed to a pressure sensitive adhesive composition which lacks functional groups containing reactive hydrogen moieties and contains no post-polymerization chemical crosslinker. The adhesive comprises, on a dry weight basis, from about 50 to about 98% of an alkyl (meth)acrylate monomer and from about 2 to about 50% of a non-cyclic nitrogen-containing monomer. The alkyl acrylate monomer is preferably a monomer having a low homopolymer glass transition temperature, such as 2-ethylhexyl acrylate and/or n-butyl acrylate. In a preferred embodiment the nitrogen-containing monomer is an N-substituted (meth) acrylamide monomer. A preferred N-substituted acrylamide for use in the practice of the invention is t-octyl acrylamide.

In another aspect of the invention the non-reactive adhesive is formulated with a therapeutic agent. The agent, while physiologically active, may or may not be pharmaceutically active.

Another aspect of the invention is directed to a transdermal drug delivery system comprising a non-reactive pressure sensitive adhesive and a therapeutic agent. In one embodiment, the adhesive serves as a carrier for the physiologically active agent.

Still another aspect of the invention is directed to a transdermal drug delivery system comprising an adhesive layer containing a therapeutic agent and a backing layer. In one embodiment, the drug delivery system also comprises a release layer. In a preferred embodiment the drug delivery system includes an adhesive layer into which the drug to be delivered is incorporated, a distal backing layer and a proximal release layer.

Yet another aspect of the invention is directed to a method of administering a therapeutic agent to a patient comprising applying to a body surface of the patient a transdermal drug delivery system comprising a non-reactive pressure sensitive adhesive and a physiologically active agent.

DETAILED DESCRIPTION OF THE INVENTION

Percent by weight means, unless expressly stated otherwise, percent dry weight.

The invention provides adhesive compositions which lack functional groups containing reactive hydrogen moieties and contain no post-polymerization chemical cross-linking. The adhesive comprises from about 50 to about 98 percent by weight of alkyl acrylate and/or alkylmethacrylate monomers and from about 2 to about 50 percent by weight of polymerizable non-cyclic nitrogen-containing monomers.

Non-reactive, as this term is used to describe the adhesive composition of the invention means that the composition lacks functional groups containing reactive hydrogen moieties, such as —COOH, —OH, and —NH$_2$.

A reactive hydrogen, as this term is conventionally used and understood in the art, means any hydrogen that can react with a Grignard reagent, see e.g., March, J., Advanced Organic Chemistry: reactions, mechanisms and structure, 4$^{th}$ edition, John Wiley & Sons, 1992, page 623.

No post-polymerization chemical cross-linking means that while monomers having multiple polymerization sites may be use to prepare the adhesive of the invention, following polymerization no reactive sites are present in the polymer.

A polymerizable non-cyclic nitrogen-containing monomer, as this term is defined and used herein, is a polymerizable monomer which must contain nitrogen, but which nitrogen may not be present within any cyclic substituent which may form a part of the monomer, i.e. the nitrogen is present in the non-cyclic portion of the monomer.

Preferred alkyl acrylates and methacrylates which may be used to practice the invention have up to about 18 carbon atoms in the alkyl group, preferably from about 4 to about 10 carbon atoms in the alkyl group. Alkyl acrylates for use in the invention include methyl acrylate, butyl acrylate, amyl acrylate, hexyl acrylate, 2-ethylhexyl acrylate, octyl acrylate, decyl acrylate, dodecyl acrylates, isomers thereof, and combinations thereof. Examples of alkyl methacrylates which may be used include methyl methacrylate, ethyl methacrylate, and isobutylmethacrylate.

The acrylic and/or methacrylic monomers are present in an amount of from about 50% by weight to about 98% by weight, preferably from about 70 to about 90% by weight, based upon the total monomer weight of the composition.

Polymerizable nitrogen-containing monomers include vinylacetamides, N-substituted acrylamides and N-substituted methacrylamides and nitriles such as methacrylonitrile or 2-cyanoethylacrylate, as well as mixtures thereof.

N-substituted acrylamides or methacrylamides include compounds having the formula:

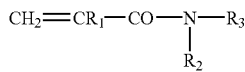

where
R$_1$ is H or CH$_3$,
R$_2$ is H, linear alkyl, branch alkyl or aromatic, and
R$_3$ linear alkyl, branch alkyl, aromatic, or a substituent of the formula:

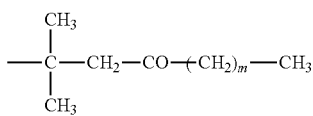

where m is 0 through 10.
Linear and branched alkyl groups are those having up to about 17 carbon atoms and include, for example, methyl, ethyl, propyl, isopropyl and the like. Aromatic substituents include, for example, benzyl, phenyl, toluyl and the like.

Examples of substituted N-substituted acrylamides for use in the practice of the invention include N-tertiary octyl acrylamide (t-octyl acrylamide), dimethyl acrylamide, diacetone acrylamide, N-tertiary butyl acrylamide (t-butyl acrylamide), N-isopropyl acrylamide (i-propyl acrylamide), N-phenyl acrylamide, and combinations thereof. Examples of N-substituted methacrylamides for use in the practice of the invention include t-octyl methacrylamide, dimethyl methacrylamide, diacetone methacrylamide, t-butyl methacrylamide, i-propyl methacrylamide, N-phenyl methacrylamide, and combinations thereof.

The polymerizable nitrogen-containing monomers are present in an amount of from about 2 to about 50% by weight, preferably from about 10 to about 30% by weight, based upon the total monomer weight of the composition.

The adhesive compositions of the present invention optionally may include other monomers including, but not limited to vinyl monomers, such as vinyl acetate and styrene, alkyl methacrylates such as methyl methacrylate and alkyl dimethacrylates.

Adhesives of the invention may also comprise blended polymers wherein the acrylic polymer is blended with and further comprises other types of polymers, including non-reactive polymers, including silicone polymers such as polydimethylsiloxane and polymethylphenylsiloxane and rubber polymers such as polyiso-butylene and styrene-isoprene-styrene block copolymer.

Preferably, the adhesive of the invention will have a glass transition temperature of less than about 10° C.

The adhesive of the invention unexpectedly maintains its adhesive properties without the need for post-polymerization crosslinking. A preferred embodiment, which gives excellent adhesive performance and excellent non-reactive performance is an adhesive copolymer composition comprising 45% by weight 2-ethylhexyl acrylate, 35% by weight methyl acrylate and 20% by weight of an N-substituted acrylamide. A preferred N-substituted acrylamide is t-octyl acrylamide.

While a particular polymerization method is described in the examples, the polymer of the present invention may be prepared by conventional polymerization methods familiar to those of skill in the art. These methods include, without limitation solution polymerization, suspension polymerization, bulk polymerization and emulsion polymerization. In the practice of the invention, it may also be advantageous to reduce the residual monomer content, or remove or reduce solvent levels and/or other volatiles, following polymerization using methods which are known and conventional in the art. Adhesive may be applied from organic solution, aqueous dispersion, or from a melt.

As used herein, the term "pressure-sensitive adhesive" refers to a viscoelastic material which adheres instantaneously to most substrates with the application of slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. While the pressure sensitive adhesive of the invention may be used in any number of applications, e.g., labels, the non-reactive nature makes the adhesive particularly well-suited for use in transdermal applications. The non-reactive pressure sensitive adhesive of the invention may be incorporated into a transdermal drug delivery device designed to deliver a therapeutically effective amount of a product to the skin of a patient, e.g., to cure a skin irritation or to deliver a therapeutically effective amount of drug across the skin of a patient.

The term transdermal refers to application on or to the skin whereby the skin is used as a portal for the administration of drugs by topical application or for diagnostic procedures, such as the monitoring of blood chemistry.

A topically applied drug may pass into and/or through the skin. The terms skin, derma and epidermis are used interchangeably unless specifically stated otherwise. Thus "transdermal" is used broadly to refer to the topical administration of a drug which acts locally, i.e., at the surface or within the skin, such as, for example, a blemish patch used to treat acne, and to the topical application of a drug which acts systemically by diffusing through the skin and entering the blood stream.

The term patient is used herein to include animals, both human and non-human, including companion animals such as dogs, cats and horses and livestock such as cattle and swine. Agricultural and horticultural applications are also contemplated.

Human patients include adults, children and infants. In terms of compliance, the transdermal drug delivery device of the invention is particularly useful in treating young children. By way of example, a patch designed for the sustained transdermal administration of methylphenidate may be applied to a young child in need of multiple daily dosing of methylphenidate. The child may then be sent to school. There is no need for additional dosing during the day, no need to disrupt school activities to administer medication, no need for adult intervention for purposes of administration and no embarrassment to the child.

The adhesive of the invention is contemplated for use in the manufacture of liquid reservoir patches and matrix patches. While the adhesive of the invention can be used in all types of transdermal drug delivery systems, it will be appreciated that the adhesive is most advantageously used with drugs containing reactive functional groups and in those systems which require that the drug diffuse through or from the adhesive. Matrix patches are particularly preferred embodiments since they are easier to manufacture than liquid reservoir patches and are more comfortable and convenient to wear.

Transdermal drug delivery devices of the invention comprise a carrier (such as liquid, gel, or solid matrix, or a pressure sensitive adhesive) into which the drug to be delivered is incorporated, a distal backing layer and a proximal release layer. When the patient peels the release liner from the adhesive and applies the patch, the drug partitions into the stratum corneum (outer skin layer) and permeates through the epidermis and dermis.

While the invention will be described in more detail in terms of a matrix-type patch, patches of the types described in Pfister et al., *Chemistry in Britain*, January 1991, pages 43-46, the disclosure of which is incorporated herein by reference, including liquid reservoir-type systems, are encompassed by the invention. Included are embodiments wherein the drug-containing polymeric phase is laminated to a pressure sensitive adhesive or used with an overlay adhesive or is the adhesive itself.

A matrix patch device according to the present invention is a unit dosage form of a drug composition in a polymeric carrier. The individual layers of the device include a substantially drug-impermeable distal backing layer, the aforementioned drug laden polymer carrier layer, also referred to herein as the carrier, and, before transdermal application, a substantially drug-impermeable proximal release layer or liner.

The portions of the carrier that are not in contact with the skin are covered by a backing. The distal backing layer, in use, defines the side of the patch that faces the environment, i.e., distal to the skin. The backing serves to protect the carrier and the components contained in the carrier, including the drug, from the environment by providing an impenetrable layer that prevents loss of the drug to the environment. Thus, the material chosen should be substantially impermeable to the drug. Advantageously, the backing material can be opaque to protect the drug from degradation from exposure to light. It may be desirable that the backing have a relatively high vapor transmission rate, since this results in the reduction of moisture buildup on the skin beneath the device and in a corresponding reduction in the amount of skin maceration that occurs. Conversely, to enhance drug flux, an occlusive backing may be selected. Further, the backing layer should be capable of binding to and supporting the other layers of the device, yet should be pliable to accommodate the movements of a person using the device since a stiff backing may cause mechanical irritation. In order to maintain the health of the covered skin during long term wear (e.g., for periods in excess of a day), it is also desirable that the backing have a relatively high permeability to oxygen. As the backing is in contact with the components of the carrier, including the drug and any excipients, it is important that the backing be stable to such components in order that the backing retains its structural integrity and conformability. It is also important that the backing not absorb the drug or excipients from the carrier. In connection with the preparation of certain reservoir type drug delivery devices, it is also desirable for the backing to be heat sealable at a relatively low temperature to a variety of other polymeric substrates.

Backings that have found use in drug delivery devices, and which can be used in the practice of this invention include, with or without modification, metal foils, metalized polyfoils, composite foils or films containing poytetrafluoroethylene (TEFLON®)-type materials or equivalents thereof, polyether block amide copolymers, polyurethanes, polyvinylidene chloride, nylon, silicone elastomers, rubber-based poylisobutylene styrene, styrene-butadiene and styrene-isoprene copolymers, polyethylene, polyester, and other such materials used in the art of transdermal drug delivery. Particularly preferred are thermoplastic polymers such as polyolefins, for example polyethylene and polypropylene, and polyesters such as polyethyleneterephthalate.

The proximal release liner or peelable film covers the skin-facing or proximal side of the device until the device is used. A silicone-coated film is typically used for such applications. Just prior to use of the device, the proximal release liner is removed to expose the drug-containing polymer layer for contact and adhesion to the skin surface. Thus, the proximal release liner is adapted to be removed from the device and should strip off the adhesive surface with minimal force.

In one embodiment, the release liner of a first patch also serves as the backing layer of a second patch. This design allows patches to be manufactured in a stacked format, and dispensed to the patient in this manner. The first patch is removed, and applied to the skin, with no excess waste generated for disposal.

The drug containing polymer layer is preferably a pressure-sensitive skin contact adhesive of the invention which is a pharmaceutically acceptable material that lacks functional groups containing reactive hydrogen moieties and forms no new functional groups upon storage. The adhesive of the invention, whether used as a carrier contact adhesive or overlay contact adhesive for transdermal patches is non-irritating, easy to apply, and easy to remove.

The term "drug" is to be construed herein in its broadest sense to mean any agent which is intended to produce some therapeutic benefit. The agent may or may not be pharmaceutically active, but will be "bioactive" in the sense that it has an effect on the human body. The agent may be used to treat or alter a condition, which may or may not be a pathological, i.e., a disease state. "Drug", "bioactive agent," "preparation," "medicament," "therapeutic agent," "physiological agent" and "pharmaceutical agent" are used interchangeably herein and include substances for use in the diagnosis, cure, mitigation, arrest, treatment or prevention of a condition or disease state or to affect the structure or function of the body. Skin-wellness agents that function to e.g., soften and moisturize are included in this term. The term "treatment" is used broadly to encompass prevention, alteration, cure and control of the condition.

The drug is present in a drug delivery device of the invention in a therapeutically effective amount, i.e., an amount effective to bring about a desired therapeutic result in the treatment of a condition to which the preparation of this invention is to be applied. Effective amount of a drug means a nontoxic but sufficient amount of a drug to provide the selected effect over a specific period of time. The amount that constitutes a therapeutically effective amount varies according to the particular drug incorporated in the device, the condition being treated, any drugs being co-administered with the selected drug, desired duration of treatment, the surface area of the skin over which the device is to be placed, and other components of the drug delivery device. Such an amount is readily determinable by the skilled practitioner.

Drugs that can be included in the carrier of the invention include substances capable of a local or a systemic effect when administered to the skin. While it will be appreciated that the invention enables the administration of drugs containing a reactive functional group, which drugs have heretofore not been able to be administered by the transdermal route using conventional acrylic adhesives, the invention is not limited to the administration of these types of drugs. Other drugs previously administered via the transdermal route using conventional acrylic adhesives or silicone adhesives may also be administered using the adhesive of the invention, either alone or in combination with another drug which may contain a reactive functional group.

Treatment areas where the delivery device of the invention finds use, and examples of pharmaceutical products which can be incorporated in the devices of the invention, include treatment for incontinence (oxybutinin), central nervous system conditions (methylphenidate), hormone therapy and birth control (estradiol, testosterone, progestin, progesterone, levonorgestrel) cardiovascular (nitroglycerin, clonidine) and cardiotonics (e.g., digitalis, digoxin), pain management or anti-inflammatory (fentanyl, lidocaine, diclofenac, flurbiprofen), cosmetic (benzoyl peroxide, salicylic acid, vitamin C, vitamin E, aromatic oils), antinauseants (scopalamine), smoking cessation (nicotine), antiinflammatory conditions, both steroidal (e.g., hydrocortisone, prednisolone, triamcinolone) and nonsteroidal (e.g., naproxen, piroxicam) treatments, antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin), antiprotazoals (e.g., metronidazole), antifungals (e.g. nystatin), calcium channel blockers (e.g. nifedipine, diltiazem), bronchodilators (e.g., theophylline, pirbuterol, salmeterol, isoproterenol), enzyme inhibitors such as collagenase inhibitors, protease inhibitors, elastase inhibitors, lipoxygenase inhibitors, and angiotensin converting enzyme inhibitors (e.g., captopril, lisinopril), other antihypertensives (e.g., propranolol), leukotriene antagonists, anti-ulceratives such as H2 antagonists, antivirals and/or immunomodulators (e.g., 1-isobutyl-1H-imidazo[4,5-c]quinolin-4-amine, 1-(2-hydroxy-2-methyl-propyl)-1H-imidazo[4,5-c]quinoline-4-amine, and acyclovir), local anesthetics (e.g., benzocaine, propofol), antitussives (e.g., codeine, dextromethorphan), antihistamines (e.g., diphenhydramine, chlorpheniramine, terfenadine), narcotic analgesics (e.g., morphine, fentanyl), cardioactive products such as atriopeptides, anticonvulsants (e.g., carbamazine), immunosuppressives (e.g., cyclosporine), psychotherapeutics (e.g., diazepam), sedatives (e.g., phenobarbital), anticoagulants (e.g., heparin), analgesics (e.g., acetaminophen), antimigrane agents (e.g., ergotamine, melatonin, sumatriptan), antiarrhythmic agents (e.g., flecainide), antiemetics (e.g., metaclopromide, ondansetron), anticancer agents (e.g., methotrexate), neurologic agents such as anxiolytic drugs, hemostatics, anti-obesity agents, and the like, as well as pharmaceutically acceptable salts, esters, solvates and clathrates thereof.

Veterinary drugs may also be conveniently applied using the transdermal drug delivery device of the invention. In addition to many of the above mentioned drugs, which can also be used in veterinary applications, additional examples include e.g., diclazuril and lufenuron.

Agricultural and horticultural agents include, for example orchid growth hormone.

It will be appreciated that transdermal drug delivery in veterinary and horticultural applications enables more exact dosing, and less waste than administration in the food/irrigation water.

The skin presents a substantial barrier to ingress of foreign substances into the body. The art has recognized that the barrier to the transdermal or percutaneous delivery of drug through the skin can be overcome or reduced by incorporating excipients into the carrier that enhance the rate at which the drug passes, i.e., penetrates, through the skin. Penetration enhancers are well-known in the art. The terms "enhancement", "penetration enhancement," and permeation enhancement" mean an increase in the permeability of a biological membrane, e.g., skin, to a drug, so as to increase the rate at which the drug permeates through the membrane and accelerate drug delivery. These agents are commonly referred to as penetration enhancers, accelerants, adjuvants and absorption promoters, and will be collectively referred to herein as "enhancers".

The drug delivery system of the invention, in addition to the drug, may advantageously also contain an effective amount of a penetration enhancer. An effective amount of a penetration enhancer means an amount that provides a selected increase in membrane permeability, rate of administration and amount of drug.

Some examples of enhancers are polyhydric alcohols such as dipropylene glycol, propylene glycol, and polyethylene glycol; oils such as olive oil, squalene, and lanolin; polyethylene glycol ethers and fatty ethers such as cetyl ether and oleyl ether; fatty acid esters such as isopropyl myristate; fatty acid alcohols such as oleyl alcohol; urea and urea derivatives such as allantoin; polar solvents such as dimethyidecylphosphoxide, methyloctylsulfoxide, dimethyllaurylamide, didecylpyrrolidone, isosorbitol, dimethylacetonide, dimethylsulfoxide, decylmethylsulfoxide, and dimethylformamide; salicylic acid; amino acids; benzyl nicotinate; bile salts; and higher molecular weight aliphatic surfactants such as lauryl sulfate salts. Other agents include oleic and linoleic acids, ascorbic acid, panthenol butylated hydroxytoluene, tocopherol, tocopheryl acetate, tocopheryl lineleate, propyloleate, isopropyl palmitate, oleamide, polyoxyethylene (4) lauryl ether, polyoxyethylene (2) oleyl ether and polyoxyethylene (10) oleyl ether sold under the trademarks Brij 30, 93 and 97 by ICI Americas, Inc., and polysorbate 20 sold under the trademark Tween 20 by ICI Americas, Inc.

Further, a plasticizer or tackifying agent can be incorporated into the adhesive composition to improve the adhesive characteristics of the adhesive composition. Some drugs, such as the vasodilator nitroglycerin, function as plasticizers in the adhesive because they are soluble to a certain degree in the polymers comprising the adhesive. For drug molecules which are not sufficiently soluble in the polymer system, a co-solvent for the drug can be added. Co-solvents, such as lecithin, retinol derivatives, tocopherol, dipropylene glycol, triacetin, propylene glycol, saturated and unsaturated fatty acids, mineral oil, alcohols, butyl benzylphthalate, and the like are useful depending on the solubility of the drug in the adhesive carrier.

A tackifying agent is particularly useful in those embodiments in which the drug and/or any excipient does not plasticize the polymer. Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) wood resins or rosins and hydrogenated forms thereof. The tackifying agent employed is preferably compatible with the blend of polymers. Silicone fluid is useful for blends comprising polysiloxane as a major component. In other embodiments, where a synthetic rubber, for example, is a major component, mineral oil is a preferred tackifying agent.

The formulated component of a transdermal patch device may also include, a controlled-viscosity composition, excipients, diluents, emollients, plasticizers, anti-irritants, opacifiers, fillers, such as clay and silica, pigments and mixtures thereof, preservatives, as well as other components or additives that are formulated for maintaining the drug composition in the polymeric layer in a drug transferring relationship with the derma, e.g., skin, as appropriate for specific applications and which is adapted to adhere to the skin at the application site.

The device of the invention is placed on the skin and allowed to remain for a time sufficient to achieve or maintain the intended therapeutic effect. The time that constitutes a sufficient time can be selected by those skilled in the art with consideration of the flux rate of the device of the invention and of the condition being treated.

The transdermal delivery devices of the invention can be made in the form of an article such as a tape, a patch, a sheet, a dressing or any other form known to those skilled in the art. The dosage system may be produced in any desirable unit form. A circular form is convenient as it contains no corners which might be easily detached from the skin. In addition to having various shapes, the dosage units produced may come in various sizes.

Generally the device will be in the form of a patch of a size suitable to deliver a preselected amount of drug through the skin. A surface area in the range of 1 to 200 $cm^2$ is contemplated and preferred sizes are 5, 10, 15, 20, 25 and 30 $cm^2$. The thickness may vary over a wide range, typically from about 1 to about 5 mil, preferably 3 to 4 mil thick. The present invention preferably incorporates enough pharmaceutically active drug to provide efficacy with a dosage system having a 5 $cm^2$ surface area and a thickness of about 3 to 4 mil.

Depending on the design of the patch and the condition to be treated, the patch will remain on the skin for up to an hour or more, up to about one week. In a preferred embodiment, the patch is designed to remain on the skin at the application site for about 24 hours, and to be changed daily. Preferably, the patch will be placed on the skin at a site different from the location of the previously used patches.

A drug delivery device of the invention can be prepared by using conventional methods to apply an appropriate carrier to the backing. For example, a matrix device can be manufactured by preparing a coating formulation by mixing a solution of the adhesive in a solvent with the drug and any excipients to form a homogeneous solution or suspension; applying the formulation to a substrate (a backing or a release liner) using well known knife or bar or extrusion die coating methods; drying the coated substrate to remove the solvent; and laminating the exposed surface to a release liner or backing.

The invention will be described further in the following examples, which are included for purposes of illustration and are not intended, in any way, to be limiting of the scope of the invention.

EXAMPLES

Pressure sensitive adhesive compositions were prepared as described in the following examples. The pressure sensitive adhesives produced were evaluated using the following adhesive test procedures
Testing Procedures
Peel 180° Peel was tested using the method described by the Pressure Sensitive Tape Council in PSTC No. 1. The test involves peeling the tape off a substrate at 180° angle after application under relatively light pressure. Testing was done to allow 20 minutes (initial peel), 24 hour and one week contact of the adhesive with the test panel. The results are reported as the force required to remove the tape, measured in ounces per inch width.
Shear Adhesion Shear adhesion was measured according PSTC No. 7 using a 1,000 gram (g) mass at room temperature. The bonded area was 1 inch×0.5 inch. The results are reported as the time required for the bond to fail.

Example 1

An initial charge containing 44.7 g 2-ethylhexylacrylate, 25.8 g methyl acrylate, 5 g t-octyl acrylamide, 69.4 g ethyl acetate (solvent), 9.8 g acetone (solvent), and 0.035 g 2,2'-azobisisobutyronitrile (AIBN) (polymerization initiator) was prepared and charged to a 1-L 4-neck round bottom flask equipped with stainless steel stirrer, thermometer, condenser, water bath, and slow addition funnels. The initial charge was heated to reflux while stirring. At 45 minutes from the start of reflux, monomer mix containing 15.3 g 2-ethylhexylacrylate, 9.2 g methyl acrylate, 11.3 g ethyl acetate and initiator mix containing 13.1 g ethyl acetate, and 0.13 g AIBN were simultaneously and uniformly added over a period of 1 hour. At 190 minutes from the start of reflux, solvent mix containing 8.1 g ethyl acetate, 12.5 g acetone was uniformly added over a period of 3 hours. At the end of the addition, the flask contents were held at reflux for 6.5 hours. At the end of the hold period, the contents were cooled to room temperature and the solution polymer discharged.

Examples 2-8

Using the general procedure described above, 7 additional adhesives were prepared by varying the amounts and/or compositions of monomers.

The major monomers and their respective amounts (in parts per hundred of total monomers weight) used to prepare the adhesives of Examples 1-8 are shown in Table 1.

TABLE 1

|  | 1 | 2 | 3 | 4 | 5 | 6 | 7 | 8 |
|---|---|---|---|---|---|---|---|---|
| t-OA |  | 5 | 0 | 0 | 0 | 20 | 0 | 0 | 0 |
| Dimethyl acrylamide | 0 | 10.8 | 0 | 0 | 0 | 0 | 0 | 0 |

TABLE 1-continued

|  | 1 | 2 | 3 | 4 | 5 | 6 | 7 | 8 |
|---|---|---|---|---|---|---|---|---|
| Isopropyl acrylamide | 0 | 0 | 12.4 | 0 | 0 | 0 | 0 | 0 |
| Vinyl acetamide | 0 | 0 | 0 | 9.3 | 0 | 0 | 0 | 0 |
| 2-ethyl hexyl acrylate | 60 | 49.6 | 48.8 | 50.4 | 45 | 75 | 75 | 50 |
| Methyl acrylate | 35 | 39.6 | 38.8 | 40.4 | 35 | 0 | 25 | 0 |
| Acrylic acid | 0 | 0 | 0 | 0 | 0 | 5 | 0 | 0 |
| Vinyl acetate | 0 | 0 | 0 | 0 | 0 | 20 | 0 | 50 |

Adhesives 1-5 are encompassed by the invention. Examples 6-8 are presented for purpose of comparison. The adhesive of Comparative Example 6 was prepared in the absence of a polymerizable nitrogen-containing monomer and contains functional groups containing reactive hydrogen moieties. The adhesives of Comparative Examples 7 and 8 were prepared in the absence of a polymerizable nitrogen containing monomer and lacks functional groups containing reactive hydrogen moieties.

Each of the adhesives of Examples 1-8 was coated on a 2-mil thick polyester film to give a 1-mil thick dry adhesive and then tested for pressure sensitive adhesive properties. Results are shown in Table 2.

TABLE 2

|  | 1 | 2 | 3 | 4 | 5 | 6 | 7 | 8 |
|---|---|---|---|---|---|---|---|---|
| Peel, 180° | | | | | | | | |
| 20 min | 44 | 54 | 55 | 27 | 57 | 60 | 43.1 | 36.5 |
| 24 hr | 44 | 59 | 61 | 53 | 59 | 75 | — | — |
| 1 week | 49 | 74 | 74 | 61 | 56 | 100 | — | — |
| Shear (hours) | 0.5 | 7.9 | 31 | 23.8 | 5 | 24+ | 0.53 (2 psi) | 0.38 |

From the data it can be seen that the adhesives of the invention, which lack functional groups containing reactive hydrogen moieties, exhibit substantially the same peel performance as Comparative Examples 6-8. In addition, the adhesives of the invention have superior shear for transdermal applications.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A composition consisting of
   an adhesive polymer prepared from a mixture of monomers consisting of:
      about 45 wt %, based on the total monomer weight, of 2-ethyl hexyl acrylate, about 35 wt %, based on the total monomer weight, of methyl acrylate, and about 20 wt %, based on the total monomer weight, of t-octylacrylamide, dimethyl acrylamide, isopropyl acrylamide, or vinyl acetamide;
   a therapeutic agent that is a non-salt; and
   at least one ingredient selected from the group consisting of enhancer, plasticizer, tackifying agent, viscosity modifier, excipient, diluent, emollient, anti-irritant, opacifier, pigment, and preservative, wherein the composition is a transdermal composition.

2. The composition of claim 1, wherein the mixture of monomers consists of 45 wt % of 2-ethylhexyl acrylate, 35 wt % of methyl acrylate and 20 wt % of t-octyl acrylamide.

3. The composition of claim 1, wherein the therapeutic agent is fentanyl.

* * * * *